United States Patent [19]

Felt

[11] Patent Number: 5,556,429
[45] Date of Patent: Sep. 17, 1996

[54] JOINT RESURFACING SYSTEM

[75] Inventor: Jeffrey C. Felt, Greenwood, Minn.

[73] Assignee: Advanced Bio Surfaces, Inc., Greenwood, Minn.

[21] Appl. No.: 239,248

[22] Filed: May 6, 1994

[51] Int. Cl.$^6$ ............................................. A61F 2/28
[52] U.S. Cl. .............................. 623/16; 623/18; 623/66; 128/898; 606/92
[58] Field of Search ........................... 623/66, 11, 16, 623/18; 606/72, 76, 77, 92, 93, 94, 213; 128/898; 433/223, 226

[56] References Cited

U.S. PATENT DOCUMENTS

| | | | |
|---|---|---|---|
| 3,223,083 | 12/1965 | Cobey | 606/76 |
| 4,203,444 | 5/1980 | Bonnell et al. | |
| 4,274,414 | 6/1981 | Johnson et al. | |
| 4,446,578 | 5/1984 | Perkins et al. | 128/1 R |
| 4,705,038 | 11/1987 | Sjostrom et al. | |
| 4,722,948 | 2/1988 | Sanderson | 523/11 |
| 4,834,729 | 5/1989 | Sjostrom | |
| 4,842,578 | 6/1989 | Johnson et al. | |
| 4,880,610 | 11/1989 | Constantz | 423/305 |
| 4,983,179 | 1/1991 | Sjostrom | |
| 5,007,940 | 4/1991 | Berg | |
| 5,064,426 | 11/1991 | Huebsch | 606/92 |
| 5,067,964 | 11/1991 | Richmond et al. | 623/18 |
| 5,082,803 | 1/1992 | Sumita | 623/16 |
| 5,130,347 | 7/1992 | Mitra | 522/149 |
| 5,171,244 | 12/1992 | Caspari et al. | |
| 5,228,459 | 7/1993 | Caspari et al. | |
| 5,258,028 | 11/1993 | Ersek et al. | 623/11 |
| 5,263,498 | 11/1993 | Caspari et al. | 128/898 |
| 5,278,201 | 1/1994 | Dunn et al. | 523/113 |
| 5,304,181 | 4/1994 | Caspari et al. | |
| 5,344,456 | 4/1994 | Nonami et al. | 623/16 |
| 5,385,469 | 1/1995 | Weissman | 433/273 |
| 5,395,376 | 3/1995 | Caspari et al. | |

OTHER PUBLICATIONS

Chapter 1, in *Biomaterials, Medical Devices and Tissue Engineering: An Integrated Approach*, Frederick H. Silver, ed., Chapman and Hall, 1994.

"New Challenges in Biomaterials", Science, 263:1715–1720 (1994), Peppas et al.

"Prevention of Postoperative Adhesions in the Rat by In Situ Photopolymerization of Bioresorbable Hydrogel Barriers," Hill–West, et al., Obstet. Gynecol. 83(1):59–64 (1994).

"Guide to Medical Plastics", pp. 41–78 in *Medical Device & Diagnostic Industry*, Apr. 1994.

"Silicones", pp. 1048–1059 in *Concise Encyclopedia of Polymer Science and Engineering*, Eds. Mark et al., Wiley and Sons, 1990.

"Hydrogels", pp. 458–459 in *Concise Encyclopedia of Polymer Science and Engineering*, Eds. Mark et al., Wiley and Sons, 1990.

Constantz, Brent R., et al., "Skeletal Repair by in Situ Formation of the Mineral Phase of Bone," *Science*, vol. 267, Mar. 24, 1995, pp. 1796–1799.

*Primary Examiner*—John G. Weiss
*Assistant Examiner*—Bruce E. Snow
*Attorney, Agent, or Firm*—Fredrikson & Byron, P.A.

[57] ABSTRACT

A system for resurfacing orthopedic joints by arthroscopic means. The system involves a method that includes the delivery of a curable biomaterial, and the use of minimally invasive means to prepare an injury site, and then deliver, cure and shape a curable biomaterial at the site of injury.

17 Claims, No Drawings

JOINT RESURFACING SYSTEM

TECHNICAL FIELD

The present invention relates to methods, apparatuses, materials and systems for the repair of musculoskeletal injury, and in particular, for bone and cartilage repair and replacement.

BACKGROUND OF THE INVENTION

The musculoskeletal system is subject to injury caused by traumatic events as well as by a number of diseases, such as osteoarthritis and rheumatoid arthritis.

Repair of connective tissue of the musculoskeletal system is commonly performed using materials such as natural or synthetic tendons and ligaments. Joint repair and replacement is typically accomplished using metal and/or polymeric implants and devices. Such devices are typically fixated into existing bone by means of bone plates, adhesives, screws, and the like.

Total joint replacement is indicated under conditions in which the cartilage surface between the bones forming a joint has degenerated. Often it has degenerated to a point where there is significant pain during locomotion, as well as during translation and rotation of joint components. This degenerative joint disease is commonly treated by a technique known as joint surface replacement arthroplasty, which involves replacement of the original surfaces with artificial weight bearing materials in the form of implants.

Hip replacement generally involves the implantation of a femoral component in the form of a ball mounted on a shaft, together with an acetabular component in the form of a socket into which the ball sits.

Total knee replacement is somewhat more difficult than hip replacement because of the complex loading pattern of the knee. The tibial component of a total knee replacement is fixed in the cancellous bone of the tibia. The femoral component is typically fixed to the cortical bone of the femoral shaft using a suitable cement.

The tibial portion of a knee prosthetic device generally involves the insertion of a broad plateau region covering the tibia, after bone of the subchondral plate is removed. In most designs, a composite material is provided, involving a metal support underlying a polymeric, or fiber-reinforced polymeric tray.

A wide array of materials have been described for use in the manufacture of medical implants. See generally, Chapter 1, in *Biomaterials, Medical Devices and Tissue Engineering: An Integrate Approach*, Frederick H. Silver, ed., Chapman and Hall, 1994. Such materials generally fall into the categories of metals, polymers, ceramics, and composite materials.

A recent article entitled "New Challenges in Biomaterials", Science, 263:1715–1720 (1994), Peppas et al., provides a useful overview of the current state of the art in biomaterials. The article describes a number of materials currently used for orthopedic applications, including metals (iron, cobalt, and titanium), degradable polymers, selfreinforced compositions of polyglycolic acid, stronger polymers such as polydioxanone, and ceramic materials such as hydroxyapatite and certain glasses.

Elsewhere, for instance at page 1719, the Peppas et al. article refers to the potential usefulness of polymers that can be triggered to undergo a phase change. The article itself does not identify such polymers, but instead postulates that materials that are initially liquid might be administered through a minimally invasive surgical device and then triggered to solidify or gel in the presence of ultraviolet light, visible light, or ionic change in vivo. As an example of this approach the article cites an article of Hill-West, et al., Obstet. Gynecol. 83(1):59–64 (1994).

The Hill-West et al. article, in turn, describes the use of a conformable, resorbable hydrogel barrier for preventing postoperative adhesions in animals. The article describes the formation of the hydrogel barrier in situ by photopolymerizing a solution of a macromolecular prepolymer using UV light. The hydrogel barrier is not described as being useful in weight-beating, orthopedic applications, and in fact, was completely resorbed within 7 days after application.

There are a number of drawbacks associated with the biomaterials and related methods presently employed for orthopedic applications, and in particular joint repair and replacement. One such drawback is that these methods generally involve invasive surgery, i.e., resecting tissue in order to gain access to the injury site. In turn, invasive surgery typically involves up to 7 to 10 days of hospitalization, with the costs associated therewith.

A related drawback of an arthrotomy involves the need to cut through skin, nerves, vessels, muscles, ligaments, tendons, and/or joint capsules. Certain procedures can also require the use of either general or spinal anesthesia. They may also require blood transfusions and signifitcant recovery time accompanied by post-surgical pain and discomfort. Lastly, prolonged physical therapy is typically required to strengthen operative areas and prevent contractures. Such therapy can often last up to six weeks or more.

It would be particularly useful to be able to repair such injuries in a manner that avoided such invasive surgical procedures and the problems associated therewith.

SUMMARY OF THE INVENTION

The present invention overcomes the drawbacks associated with the prior art by providing a method, system and related components for repairing or resurfacing the site of injured orthopedic tissue by minimally-invasive means.

The method of the present invention comprises the steps of:

(a) providing a curable biomaterial; and
(b) employing minimally invasive means to:
  (i) prepare the tissue injury site for receipt of the biomaterial;
  (ii) deliver a quantity of the curable biomaterial to the prepared tissue injury site;
  (iii) cure the delivered biomaterial in such a manner that the cured biomaterial is permanently retained in apposition to the prepared site; and
  (iv) contour the cured, retained biomaterial to achieve a desired conformation approximating that of natural tissue.

The method of the invention lends itself to a corresponding system that comprises curable biomaterial, in combination with minimally invasive means for preparing the tissue site; delivering the biomaterial to the prepared tissue site; curing the biomaterial in situ; and contouring the cured biomaterial. The individual components of such a system, and particularly means for delivering and curing biomaterial in a minimally invasive fashion are considered novel as well.

In a preferred embodiment, a system is provided that comprises: (a) an arthroscopic surgical instrument; and (b) a fluid delivery cannula capable of delivering a flowable, curable biomaterial under arthroscopic visualization, the biomaterial comprising a curable polymer and hydrogel.

The preferred system can be used to perform a method that comprises the steps of:

(a) providing a flowable, curable biomaterial comprising a curable polymer and hydrogel;

(b) preparing the tissue injury site by operation of the arthroscopic instrument, and under arthroscopic visualization;

(c) preparing a tissue access site and inserting and directing the delivery cannula through the tissue access site to the site of tissue injury;

(d) delivering a quantity of the curable biomaterial through the cannula to the prepared site;

(e) curing the delivered biomaterial by minimally invasive means and in a manner such that the cured biomaterial is retained in apposition to the prepared site; and (f) contouring the cured biomaterial to achieve a desired conformation approximating that of natural tissue.

In an alternative embodiment, the cured, shaped biomaterial can be treated or modified in order to improve one or more desirable properties, for instance, it can be coated with a permanent interface material in order to improve the biocompatibility or coefficient of friction of the final implant.

DETAILED DESCRIPTION

As used herein the following words and terms shall have the meanings ascribed below:

"biomaterial" refers to a material that is capable of being introduced to the site of an orthopedic tissue injury by minimally invasive means, and there be cured or otherwise modified in order to cause it to be retained in a desired position and configuration. Generally such biomaterials are flowable in their uncured form, meaning they are of sufficient viscosity to allow their delivery through a cannula of on the order of about 2 mm to about 6 mm inner diameter, and preferably of about 3 mm to about 5mm inner diameter. Such biomaterials are also curable, meaning that they can be cured or otherwise modified, in situ, at the tissue site, in order to undergo a phase or chemical change sufficient to retain a desired position and configuration.

"minimally invasive means" refers to surgical means, such as arthroscopic surgical means, that can be accomplished without the need to resect tissue in order to gain access to a site of orthopedic injury.

"arthroscopic surgical instrument" shall refer to the controllers and associated hardware and software necessary for performing conventional arthroscopic surgery;

"delivery cannula" shall mean a cannula capable of being operated in a minimally invasive fashion under arthroscopic visualization, together with associated connective tubing and containers for the operable and fluid attachment of the cannula to a source of biomaterial for the storage, delivery, and recovery of biomaterials of the present invention;

According to a preferred embodiment, a liquid phase polymer-hydrogel composite is applied through a cannula under arthroscopic visualization. The composite is cured and contoured in situ to effectively resurface a damaged joint. The cured polymer-hydrogel composite exhibits physical/ chemical characteristics analogous to those of human cartilage, and demonstrates an optimal combination of such properties as load bearing, shear stress resistance, impact absorption, and wear characteristics. The surface of the cured composite can optionally be modified after curing and contouring, e.g., in order to reduce its coefficient of friction.

In a preferred embodiment, the method of the present invention comprises the step of providing a curable biomaterial comprising a curable polymer and hydrogel combination. Biomaterials suitable for use in the present invention include those materials that are capable of being delivered by means of a cannula, as described herein, and cured in situ in order to form a replacement material for bone or cartilage.

Natural cartilage is a non-vascular structure found in various parts of the body, and particularly articular cartilage, which exists as a finely granular matrix forming a thin incrustation on the surfaces of joints. Its natural elasticity enables it to break the force of concussions, while its smoothness affords ease and freedom of movement. In terms of thickness, cartilage tends to take on the shape of the articular surface on which it lies. Where this is convex, the cartilage is thickest at the center, where the greatest pressure is received. The reverse is generally true in the case of concave articular surfaces.

Preferred biomaterials are intended to mimic many of the physical-chemical characteristics of natural cartilage. Preferred biomaterials are composites of two or more individual materials, and particularly those comprising two phase systems formed from a polymeric matrix and a hydrogel filler.

Common polymeric materials for use in medical devices include, for example, polyvinyl chlorides, polyethylenes, stryrenic resins, polypropylene, thermoplastic polyesters, thermoplastic elastomers, polycarbonates, acrylonitrile-butadiene-styrene ("ABS") resins, acrylics, polyurethanes, nylons, styrerie acrylonitriles, and cellulosics. See, for example, "Guide to Medical Plastics", pages 41–78 in *Medical Device & Diagnostic Industry*, April, 1994, the disclosure of which is incorporated herein by reference.

Suitable matrix materials for use in the present invention are those polymeric materials that provide an optimal combination of properties relating to their manufacture, application, and in vivo use. In the uncured state, such properties include processability and the ability to be stably sterilized and stored. In the course of applying such material, such properties include hydrogel compatibility and capacity, flowability, and in vivo curability. In the cured state, such properties include moldability, cured strength (e.g., tensile and compressive), elongation to break, and biocompatability. Examples of suitable matrix materials include, but are not limited to, silicone polymers and polyurethane polymers.

In a preferred embodiment, the matrix is formed of a silicone polymer, i.e., polymer containing a repeating silicon-oxygen backbone together with organic R groups attached to a significant portion of the silicon atoms by silicon-carbon bonds. See generally, "Silicones", pages 1048–1059 in *Concise Encyclopedia of Polymer Science and Engineering*, Eds. Mark et al., Wiley and Sons, 1990, the disclosure of which is incorporated herein by reference.

Silicone polymers are commercially available in at least three general classes, namely as homopolymers, silicone random polymers, and silicone-organic (block) copolymers. Homopolymers in the form of polydimethyl siloxanes are preferred, and constitute the largest volume of homopolymers produced today.

In an alternative preferred embodiment, the matrix is formed of a polyurethane polymer. Polyurethanes, e.g, thermoplastic polyurethanes ("TPU"), are typically prepared using three reactants: an isocyanate, a long-chain macrodiol, and a short-chain diol extender. The isocyanate and long-chain diol form a "soft" segment, while the isocyanate and short-chain diol form a "hard" segment. It is the interaction of soft and hard segments that determines and provide the polymer with rubber-like properties.

During melt processing, the polyurethane chains are linear and assume the configuration into which they are formed, such as by injection molding, or in the case of the present invention, by arthroscopic application. On cooling, the hard segments form ordered domains held together by hydrogen bonding. These domains act as cross-links to the linear chains, making the material similar to a cross-linked rubber.

Those skilled in the art, in view of the present invention, will appreciate the manner in which the choice of isocyanate, macrodiol, and chain extender can be varied to achieve a wide diversity of properties. Preferred TPU's for medical use are presently based on the use of a diisocyanate such as diphenylmethane diisocyanate ("MDI"), a glycol such as polytetramethylene ether glycol, and a diol such as 1,4-butanediol.

Hydrogels suitable for use in composites of the present invention are water-containing gels, i.e., polymers characterized by hydrophilicity and insolubility in water. See, for instance, "Hydrogels", pages 458–459 in *Concise Encyclopedia of Polymer Science and Engineering*, Eds. Mark et al., Wiley and Sons, 1990, the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels assist the cured composite with load bearing capabilities of the cured composite. They also tend to decrease frictional forces on the composite and add thermal elasticity.

In a preferred embodiment, the hydrogel is a fine, powdery synthetic hydrogel. Suitable hydrogels exhibit an optimal combination of such properties as compatibility with the matrix polymer of choice, and biocompatability.

Suitable hydrogels swell to an equilibrium volume in water, but preserve their shape. Synthetic hydrogels suitable for use in forming a composite of the present invention include those based on methacrylic and acrylic esters, (meth)acrylamide hydrogels, and those based on N-vinyl-2-pyrrolidinone.

Preferred hydrogels include those formed from monomeric hydroxyalkyl acrylates and methacrylates, copolymerized with a suitable cross-linking agent, such as ethylene dimethacrylate ("EDMA").

In a particularly preferred embodiment the matrix polymer is a siloxane (i.e., silicone polymer), and preferably one selected from the group consisting of alpha, omega-dihydroxypoly(dimethylsiloxane) and poly(dimethylsiloxane) with 0.2 mol % of vinylmethyl-siloxane units. Dispersed as the hydrogel component in the preferred polymer is 15% to 30% by weight based on the weight of the uncured composite) of a lightly cross-linked hydrogel aggregate. A preferred hydrogel aggregate is formed by 2-hydroxyethyl methacrylate (HEMA) cross-linked by ethylene dimethacrylate (EDMA) at a concentration of 2%–5% by weight, based on the weight of the hydrogel.

Those skilled in the art will appreciate the manner in which hydrogel/matrix combinations and concentrations can be altered based on their intended application. For instance, a stiffer composite with a low hydrogel concentration, e.g., ~ 10% based on the final weight of the composite, would be suitable for intervertebral disc replacement.

Depending, for instance, on their intended application, biomaterials will preferably contain a hydrogel phase at a concentration of between about 15 and 50 weight percent, and preferably between about 10 and about 50 weight percent, and preferably between about 15 and about 30 weight percent, based on the weight of the combination of matrix and hydrogel.

Composites of the present invention can also include other optional adjuvants and additives, such as stabilizers, fillers, antioxidants, catalysts, plasticizers, pigments, and lubricants, to the extent such optional ingredients do not diminish the utility of the composition for its intended purpose.

Cured polymer-hydrogel composites demonstrate an optimal combination of physical/chemical properties, particularly in terms of their conformational stability, dissolution stability, biocompatability, and physical performance, e.g., physical properties such as density, thickness, and surface roughness, and mechanical properties such as load-bearing strength, tensile strength, static shear strength, fatigue of the anchor points, impact absorption, wear characteristics, and surface abrasion. Such performance can be evaluated using procedures commonly accepted for the evaluation of natural tissue and joints, as well as the evaluation of biomaterials.

In particular, preferred composite materials, in the cured form, exhibit mechanical properties approximating those of the natural tissue that they are intended to replace. For instance, preferred cured composites exhibit a load bearing strength of between about 50 and about 200 psi (pounds per square inch), and preferably between about 100 and about 150 psi. Such composites also exhibit a shear stress of between about 10 and 100 psi, and preferably between about 30 and 50 psi, as such units are typically determined in the evaluation of natural tissue and joints.

Preferred biomaterials are also stable under conditions used for sterilization, and additionally are stable on storage and in the course of delivery. They are also capable of flowing through a delivery cannula to an in vivo location, and being cured in situ, as by exposure to an energy source such as ultraviolet light or by chemical reaction. Thereafter the cured biomaterial is suitably amenable to shaping and contouring, by the use of conventional or custom designed arthroscopic tools or instruments. Over the course of their use in the body the cured, contoured biomaterial exhibits physical-chemical properties suitable for use in extended in vivo applications.

As another step of the method of the invention, the tissue injury site is prepared for receipt of the biomaterial. Those skilled in the art will appreciate the manner in which computer analysis of subchondral bone mass can allow the operator to customize the mechanical properties of the polymer-hydrogel composite to match the adjacent subchondral bone. This can be accomplished by adjusting the size of the hydrogel aggregates and by changing the percentage of the hydrogel in the polymer composite.

In a preferred method, the patient is first prepped and draped as per routine arthroscopic procedure. The first area to by resurfaced is then positioned horizontally and facing upright. If the opposing bone requires resurfacing the joint can be repositioned after the initial application has cured. This will allow gravity to assist in filling the anchor points and distributing the liquid composite evenly over the surface to be covered. Based on the present description, all the necessary maneuvers will typically be carried out using only two or three access portals.

The surface to be bonded is first cleaned of inflammatory synovia and frayed or damaged cartilage using a laser knife and/or other instruments, such as an arthroscopic shaver. The surface is then be prepared in order to improve its ability to accept and retain biomaterial. For instance, the subchondral bone is roughened by a burr and any osteophytes removed, also by the use of a burr. The bone is then irrigated to remove debris and the site suctioned dry. The bone can also be abraded in order to roughen its surface, or it can be coated with a suitable cement or other interface material.

In a preferred embodiment, anchoring points are created in the supporting joint tissue. For instance, inverted T-shaped (⊥) anchor points can be cut into the subchondral bone using specially designed arthroscopic drill bits or by laser means.

If only a small patch is needed only one or two anchor points may be sufficient, providing the number and arrangement of points is sufficient to prevent rotational or translational movement of the cured biomaterial.

If a larger area of cartilage is being replaced, then six to nine anchor points may be necessary. The number, size and location of sites can be determined on a case by case basis, by balancing the need to retain the cured biomaterial in permanent engagement with the natural tissue, with the need to avoid undue trauma or damage to the structural integrity of the natural tissue itself. Additional or other means, for instance the use of cements, can also be used to enhance the permanent engagement of the cured biomaterial with the natural joint tissue.

For instance, the prepared bone surface, including the anchor sites, can be treated with high molecular weight hyaluronic acid. This will improve adhesion of the polymer and act to inhibit inflammation and local osteoporosis. High molecular weight hyaluronic acid has also been shown to be an effective stimulator of osteophytes (i.e., bone-forming cells) as well as an inhibitor of Interleukin-1 (I1-1). As an IL-1 inhibitor, the acid will tend to decrease the inflammatory response in the area around the new insert.

As another step of the invention, a desired quantity of the curable biomaterial is delivered by minimally invasive means to the prepared site. Uncured biomaterial, either in bulk or in the form of separate reactive components, can be stored in suitable storage containers, e.g., sterile, teflon-lined metal canisters. The biomaterial can be delivered, as with a pump, from a storage canister to the delivery cannula on demand. Biomaterial can be delivered in the form of a single composition, e.g., including both polymer matrix and hydrogel, or can be delivered in the form of a plurality of components or ingredients. For instance, polymer matrix and hydrogel can be separately stored and suitably mixed or combined either in the course of delivery or at the injury site itself.

An example of a delivery system that can serve as a model for the delivery of uncured biomaterials is one presently sold by Dyonics, Inc. as the "InteliJET Fluid Management System". This system involves the a low pressure, high flow rate delivery of saline to a site, and combines delivery with suction that is automatically adjusted to specific blade styles.

In terms of its component parts, a preferred delivery system of the present invention will typically include a motor drive unit, with a remote controller, associated tube sets, a nonscope inflow delivery cannula, having independent fluid dynamics pressure and flow rate adjustments, an energy source for curing, attachments for the flush, vacuum, waste canister, overflow jars.

The application cannula will then be inserted into the joint and under visualization from the fiberoptic scope the polymer composite will be applied to the subchondral bone. The flow of the liquid phase polymer composite will be controlled by the operator via a foot pedal connected to the pumping mechanism on the polymer canister. The liquid phase polymer composite will flow from the tip of the application catheter to fill the anchor points and subsequently cover the subchondral bone.

As another step of the invention, the delivered biomaterial is cured by minimally invasive means and in such a manner that the cured biomaterial is retained in apposition to the prepared site. As described herein, the biomaterial can be cured by any suitable means, either in a single step or in stages as it is delivered. Preferred biomaterials are curable by the application of ultraviolet light, making them particularly amenable to a system that delivers such light by minimally invasive means.

When a sufficient amount of uncured biopolymer has been delivered, polymerization can be initiated by any suitable means, e.g., by the use of an ultraviolet light source at the tip of the application cannula. After the composite has cured (polymerized) the surface can be contoured as needed by other arthroscopic instruments. The joint will then be irrigated and the instruments removed from the portals.

Using the preferred composite materials described herein it is envisioned that there may be some natural migration of the hydrogel component to the composite surface in the course of curing. This migration will tend to produce a net positive charge across the surface of the composite. This positive charge, in turn, will tend to bind negatively charged hyaluronic acid, which is a compound that naturally occurs in the joint (produced by Type A synoviocytes). While not intending to be bound by theory, it would appear that the result of such binding will produce a lubricating effect to the surface of the composite. Since the hyaluronic acid is a normal product of the synovial lining cell it will be continuously replenished. A synthetic hydrophilic bilayer may alternatively be applied to reduce the coefficient of friction further.

The steps of preparing the joint surface and contouring the cured biomaterial, as described herein, can be accomplished using conventional arthroscopic instruments and tools. Stryker, Inc., Zimmer, Inc. and Dyonics, Inc. for instance, produce a wide array of arthroscopic surgical blades and instruments. Representative products are described in Dyonics' U.S. Pat. Nos. 4,274,414, 4,203,444, 4,705,038, 4,842,578, 4,834,729, and 4,983,179, the disclosure of each of which is incorporated herein by reference.

In yet another step of the present invention, the cured, retained biomaterial is contoured to achieve a desired conformation approximating that of natural tissue.

The preferred composite is heat moldable, allowing for sculpting with a probe that can be introduced through an arthroscopic portal. Such a probe will typically have a retractable, flat spatula-shaped end. The tip of the spatula can be heated to about 100 degrees centigrade, at which temperature the surface of the composite can be sculpted to the desired contour. As the composite cools, it will have sufficient memory to retain the shape it was given.

If unusual wear occurs in a given area, the implant can later be resculpted to cover the worn area without the need to repeat the entire process described above. Instead, the heat probe can simply be re-inserted under the arthroscopic visualization and the insert remolded to provide adequate size or properties in the needed area.

The steps described herein can be performed or combined in any suitable fashion. For instance, it is contemplated that the delivery, curing and contouring of biomaterial can be accomplished simultaneously and in a single step, for instance, by the use of a mold that retains a biomaterial in a desired shape as it is delivered and cured.

Optionally, and preferably, the final biomaterial can be subjected to further physical/chemical modifications, e.g., in order to enhance it performance, biocompatability, and the like. For instance, calcitonin and inflammatory inhibiting molecules such as Interleuken I inhibitors can be attached to the bone composite surface to prevent local osteoporosis and local inflammatory response which cause loosening. Similarly, the surface of the cured composite can optionally be modified in order to reduce the coefficient of friction.

In a preferred embodiment, a computer program can be used that is based on existing and ideal articulation angles. The program can assist the operator in producing a component having an optimal combination of physical characteristics, for instance contour and thickness, in order to provide optimal alignment of the involved joint.

Similarly, a holographic image can be generated through the arthroscope to aid the operator in producing the optimal thickness and contour of the polymer composite. Small joint applications, e.g., for wrists and ankles, as well as for metacarpal phalangeal joints, proximal interphalangeal joints, metatarsal phalangeal joints, and first carpalmetacarpal joints can also be developed.

What is claimed is:

1. A method for repairing or resurfacing the site of an injured articulating joint, the method comprising the steps of:
    (a) providing a curable biomaterial; and
    (b) performing the surreal steps of;
        (i) accessing and preparing the joint site for receipt of the biomaterial;
        ii) delivering a quantity of the curable biomaterial to the prepared joint site;
        (iii) curing the delivered biomaterial in such a manner that the cured biomaterial is permanently retained in apposition to the prepared site; and contouring the cured, retained biomaterial to achieve a desired conformation approximating that of the natural joint, wherein steps (i) through (iii) are each performed using minimally invasive surgical means.

2. A method according to claim 1 wherein the curable biomaterial comprises a polymeric matrix and hyrdrogel combination.

3. A method according to claim 2 wherein the polymeric matrix is selected from the group consisting of silicone polymers and polyurethane polymers.

4. A method according to claim 1 wherein the minimally invasive surgical means are arthroscopic means.

5. A method according to claim 4 wherein the delivery step is performed under arthroscopic visualization using a cannula suitably dimensioned to deliver the curable biomaterial.

6. A method according to claim 1 comprising the further step of coating or modifying the surface of the contoured material with a permanent interface material in order to improve the biocompatability or coefficient of friction of the cured biomaterial, wherein the coating or modifying step is also performed using minimally invasive surgical means.

7. A method according to claim 1 wherein the biomaterial comprises a curable polyurethane polymer.

8. A method according to claim 7 wherein the polyurethane comprises isocyanate, long-chain macrodiol, and short-chain diol extender components.

9. A method according to claim 8 wherein the isocyanate component comprises a diisocyanate.

10. A method according to claim 9 wherein the diisocyanate comprises diphenylmethane diisocyanate.

11. A method according to claim 8 wherein the long-chain macrodiol component comprises a glycol.

12. A method according to claim 11 wherein the glycol comprises polytetramethylene ether glycol.

13. A method according to claim 8 wherein the short-chain diol component comprises 1,4-butanediol.

14. A method according to claim 1 wherein the delivery step is performed using an arthroscopic cannula.

15. A method according to claim 1 wherein the minimally invasive surgical steps are each performed through access portals and under visualization with a fiberoptic scope.

16. A method for repairing or resurfacing the site of an injured articulating joint, the method comprising the steps of:
    (a) providing a flowable, curable biomaterial; hydrogel;
    (b) preparing an access site by means of an arthroscopic system comprising a fiberoptic scope and a biomaterial delivery cannula and inserting and directing a delivery cannula through the tissue access site to the site of joint injury;
    (c) delivering a quantity of the curable biomaterial through the cannula to the prepared joint site;
    (d) curing the delivered biomaterial in such a manner that the cured biomaterial is retained in apposition to the prepared joint site; and
    (e) contouring the cured biomaterial to achieve a desired conformation approximating that of the natural joint, wherein steps (b) through (e) are each performed using minimally invasive surgical means.

17. A method according to claim 16 comprising the further step of coating or modifying the surface of the contoured material with a permanent interface material in order to improve the biocompatibility or coefficient of friction of the cured biomaterial, wherein the coating or modifying step is also performed using minimally invasive surgical means.

* * * * *

UNITED STATES PATENT AND TRADEMARK OFFICE
CERTIFICATE OF CORRECTION

PATENT NO. : 5,556,429
DATED : September 17, 1996
INVENTOR(S) : Jeffrey C. Felt

It is certified that error appears in the above-indentified patent and that said Letters Patent is hereby corrected as shown below:

Column 1, line 50, replace "*Integrate*" with --*Integrated*--.

Column 1, line 60, replace "selfreinforced" with --self-reinforced--.

Column 2, line 13, replace "beating" with --bearing--.

Column 4, line 33, replace "styrerie" with --styrene--.

Column 9, line 26, replace "surreal" with --surgical--.

Column 9, line 39, replace "hyrdrogel" with --hydrogel--.

Signed and Sealed this

Twenty-first Day of October 1997

Attest:

BRUCE LEHMAN

Attesting Officer

Commissioner of Patents and Trademarks